(12) United States Patent
Fukuzawa

(10) Patent No.: US 7,919,659 B2
(45) Date of Patent: Apr. 5, 2011

(54) CATALYST FOR CYCLOOLEFIN PRODUCTION AND PROCESS FOR PRODUCTION

(75) Inventor: Akiyoshi Fukuzawa, Kurashiki (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 960 days.

(21) Appl. No.: 11/570,367

(22) PCT Filed: Mar. 29, 2005

(86) PCT No.: PCT/JP2005/005844
§ 371 (c)(1),
(2), (4) Date: Dec. 11, 2006

(87) PCT Pub. No.: WO2006/006277
PCT Pub. Date: Jan. 19, 2006

(65) Prior Publication Data
US 2008/0064908 A1    Mar. 13, 2008

(30) Foreign Application Priority Data

Jul. 9, 2004  (JP) .................................. 2004-202887

(51) Int. Cl.
C07C 5/11  (2006.01)
(52) U.S. Cl. ........ 585/269; 585/250; 585/266; 585/271; 585/273; 502/325; 502/328; 502/329
(58) Field of Classification Search ................. 585/268, 585/269, 273; 502/325
See application file for complete search history.

(56) References Cited

U.S. PATENT DOCUMENTS

| | | | |
|---|---|---|---|
| 4,575,572 A |  | 3/1986 | Ichihashi et al. |
| 4,734,536 A | * | 3/1988 | Nagahara et al. ............. 585/269 |
| 5,128,291 A | * | 7/1992 | Wax et al. .......................... 502/8 |
| 5,145,816 A |  | 9/1992 | Beck et al. |
| 5,157,179 A | * | 10/1992 | Setoyama et al. ............ 585/266 |
| 5,334,790 A |  | 8/1994 | Richard et al. |
| 5,569,803 A | * | 10/1996 | Takewaki et al. ............. 585/269 |
| 5,656,761 A | * | 8/1997 | Nagahara et al. ............. 585/269 |
| 5,969,202 A |  | 10/1999 | Ashida et al. |
| 6,248,924 B1 |  | 6/2001 | Rühl et al. |

FOREIGN PATENT DOCUMENTS

| | | |
|---|---|---|
| CN | 1174753 | 3/1998 |
| JP | 52-3933 | 1/1977 |
| JP | 57-130926 | 8/1982 |
| JP | 61-040226 | 2/1986 |
| JP | 61-050930 | 3/1986 |
| JP | 62-045541 | 2/1987 |
| JP | 62-045544 | 2/1987 |
| JP | 62-201830 | 9/1987 |
| JP | 63-017834 | 1/1988 |
| JP | 63-063627 | 3/1988 |
| JP | 63-243038 | 10/1988 |
| JP | 4-074141 | 3/1992 |
| JP | 52-054827 | 10/1993 |
| JP | 7-285892 | 10/1995 |
| JP | 11-222447 | 8/1999 |
| JP | 2002-154990 | 5/2002 |
| TW | 222262 | 3/1993 |
| TW | 385303 | 3/2000 |
| TW | 460435 | 10/2001 |

OTHER PUBLICATIONS

J. Wang, et. al. "Partial Hydrogenation of Benzene to Cyclohexene on a Ru-Zn/m-ZrO2 Nanocomposite Catalyst" in Applied Catalysis A: General 272 (2004) 29-36.*
J. L. Blin, et. al. ("Mesoporous Zirconium Oxides: An Investigation of Physico-chemical Synthesis Parameters" in Studies in Surface Science and Catalysis, 141, pp. 257-264, A. Sayari and M. Jaroniec, (eds.), Elsevier, 2002.*
Shalliker, et. al. ("Examination of Various Pore Size Zirconias for Potential Chromatographic Applications" in Powder Technology, 91 (1997) 17-23).*
Wang, et al., "Partial Hydrogenation of Benzene to Cyclohexene on a Ru-Zn/m-ZrO2 Nanocomposite Catalyst" in Applied Catalysis A: General, 272 (2004) 29-36.*
English Language Abstract of JP 63-243038.
English Language Abstract of JP 7-285892.
English Language Translation of the Claims of JP 52-3933.
English Language Abstract of JP 61-050930.
English Language Abstract of JP 62-045541.
English Language Abstract of JP 62-045544.
English Language Abstract of JP 62-201830.
English Language Abstract of JP 63-017834.
English Language Abstract of JP 63-063627.
English Language Abstract of JP 57-130926.
English Language Abstract of JP 61-040226.
English Language Abstract of JP 4-074141.
English Language Abstract of JP 2002-154990.
English Language Abstract of JP 52-054827.
English language abstract of JP 11-222447.
English language abstract of TW 460435.
English language abstract of TW 222262.
Blin et al., "Synthesis and Characterization of Nanostructured Mesoporous Zirconia Catalyst Supports Using Non-Ionic Surfactants as Templating Agents", Studies in Surface Science and Catalysis 143, pp. 1035-1043 (2002).

* cited by examiner

*Primary Examiner* — Glenn A Caldarola
*Assistant Examiner* — Bradley Etherton
(74) *Attorney, Agent, or Firm* — Greenblum & Berstein, PLC

(57) ABSTRACT

A catalyst for production of a cycloolefin by partial hydrogenation of a monocyclic aromatic hydrocarbon, wherein the catalyst comprises zirconia as a carrier, and particles having an average primary particle diameter in a range of from 3 to 50 nm and an average secondary particle diameter in a range of from 0.1 to 30 μm.

14 Claims, No Drawings

CATALYST FOR CYCLOOLEFIN PRODUCTION AND PROCESS FOR PRODUCTION

TECHNICAL FIELD

The present invention relates to a catalyst for production of cycloolefins by the partial hydrogenation of a monocyclic aromatic hydrocarbon, a process for production of the catalyst and a process for production of cycloolefins. Specifically, the present invention relates to a catalyst for production of cycloolefins, formed so that the catalyst comprises zirconia as a carrier, and has an average primary particle diameter from 3 to 50 nm and an average secondary particle diameter from 0.1 to 30 μm. Additionally, the present invention relates to a process for production of the catalyst and a process for production of cycloolefins, characterized in that the catalyst is used for the partial hydrogenation in the liquid phase of a monocyclic aromatic hydrocarbon in the presence of water.

BACKGROUND ART

Conventionally, a ruthenium catalyst has generally been employed as the catalyst for producing cycloolefins through the partial hydrogenation of a monocyclic aromatic hydrocarbon. Further, for such ruthenium catalysts, processes typically used water and a metal salt. As production processes using a well-known catalyst, examples of processes which carry out a reaction by using fine particles of ruthenium metal unchanged are disclosed in patent documents 1 to 3. Examples of processes which carry out a reaction by adding at least one kind of metal oxide in addition to fine particles of ruthenium metal are disclosed in patent documents 4 to 6. Examples of processes which employ a catalyst supporting ruthenium on a carrier of silica, alumina, silica-zirconia and the like are disclosed in patent documents 7 to 10. Additionally, an example of a process which employs a catalyst supporting ruthenium on a mesoporous silica material is disclosed in patent document 11.

The conventional processes, however, have a number of problems. In the case of carrying out a reaction by using fine particles of ruthenium metal unchanged as the catalyst, or the case of carrying out a reaction by adding at least one kind of metal oxide in addition to fine particles of ruthenium metal, catalytic activity decreases due to agglomeration of the catalyst particles in the reaction system. Thus, cycloolefin productivity is decreased.

On the other hand, catalysts having ruthenium loaded on a carrier of silica, alumina, silica-zirconia or the like have a problem in that its selectivity for cycloolefin is very low, although it is initially highly active with respect to ruthenium. Another problem exists in that the carrier dissolves under reaction conditions where water and a metal salt are present (hydrothermal and acidic). Dissolution of the carrier causes peeling of the supported active hydrogenation component from the carrier, which leads to a dramatic decrease in activity and a drop in selectivity. An additional problem arises in that the eluted carrier contaminates the reaction system. For these reasons, there is a demand for a technology which can stabilize catalytic performance and stably maintain the reaction system.

[Patent Document 1] JP-A-61-50930
[Patent Document 2] JP-A-62-45541
[Patent Document 3] JP-A-62-45544
[Patent Document 4] JP-A-62-201830
[Patent Document 5] JP-A-63-17834
[Patent Document 6] JP-A-63-63627
[Patent Document 7] JP-A-57-130926
[Patent Document 8] JP-A-61-40226
[Patent Document 9] JP-A-4-74141
[Patent Document 10] JP-A-7-285892
[Patent Document 11] JP-A-2002-154990

DISCLOSURE OF THE INVENTION

Problems to be Solved by the Invention

One characteristic of the present invention is its use as a carrier of zirconia which does not dissolve even under the hydrothermal and acidic reaction conditions that are present in cycloolefin production. Using a carrier that does not dissolve allows the carrier to remain as a solid even if the reaction system is a liquid phase. This is advantageous in that the reaction system is not contaminated and that the carrier can be handled easily when separating/recovering it.

Even if a carrier that does not dissolve under hydrothermal and acidic reaction conditions is used, physical properties of the catalyst change during the preparation of the catalyst or under the reaction conditions depending on the physical properties of the carrier used. Peeling or agglomeration of the catalyst component on the carrier may occur, thereby causing a decrease in activity or selectivity. Furthermore, if the reaction temperature or pressure is high, the decrease in catalytic performance increases has a greater impact. Additionally, the size of the catalyst or carrier particles influences the reaction performance of the catalyst as well as dispersion and handleability.

While catalyst dispersion within the reaction system improves if the catalyst particles are small, separation and recoverability worsen because the catalyst particles are so fine. On the other hand, while separation and recoverability improve if the catalyst particles are large, the large particles can cause other problems. Such problems include, for example, causing a reduction in crushing strength or a reduction in reaction performance. The support component for supporting onto the carrier is small in comparison to the carrier weight. Usually, the size of the catalyst particles is generally equal to the size of the carrier. The catalyst for cycloolefin production according to the present invention, however, can have its physical properties change depending on the characteristics that the carrier possesses, as the catalyst preparation process and employed reaction conditions are hydrothermal and acidic conditions. For this reason, it is necessary to define the catalyst particles. In addition, the carrier must not only not dissolve under the conditions used, but it must also possess the physical properties of improving catalytic performance and being able to stably maintain the catalyst component on the carrier, as well as being excellent in handleability.

The present invention defines composition parameters, such as the size of catalyst particles. It is an object of the present invention to provide a catalyst for cycloolefin production which possesses high activity and high selectivity for its catalytic performance and which also improves catalyst life and handleability through the use of a defined carrier.

Means to Solve the Problems

As a result of earnest research for achieving the above-described object, the present inventors have found that the below-described catalyst exhibits high performance in the areas of activity, selectivity, life stability and handleability during production of a cycloolefin by partial hydrogenation of a monocyclic aromatic hydrocarbon. Based on this finding, the present inventors have completed the present invention. That is, the present invention is directed to the following:

(1) A catalyst for production of a cycloolefin by partial hydrogenation of a monocyclic aromatic hydrocarbon, wherein the catalyst comprises zirconia as a carrier, and particles having an average primary particle diameter in a range of from 3 to 50 nm and an average secondary particle diameter in a range of from 0.1 to 30 μm.

(2) The catalyst according to the above-described (1), wherein the catalyst has an average pore diameter in a range of from 2.5 to 15 nm, and a pore volume in the 2.5 to 15 nm range of the pore diameter is 50% by volume or more of the total pore volume having pore diameters from 2 to 150 nm.

(3) The catalyst according to the above-described (1) or (2), wherein the catalyst contains ruthenium.

(4) The catalyst according to the above-described (3), wherein the average crystallite diameter of the ruthenium is from 2 to 15 nm (5) The catalyst according to the above-described (3) or (4), wherein the catalyst comprises zinc or a zinc compound.

(6) The catalyst according to any of the above-described (1) to (5), wherein the catalyst has a specific surface area in a range of from 20 to 300 $m^2/g$.

(7) The catalyst according to any of the above-described (1) to (6), wherein the carrier is an interstitial-pore type porous zirconia material formed by assemblage of the primary particles.

(8) The catalyst according to the above-described (7), wherein the carrier is a hafnium oxide-containing zirconia.

(9) A production process of a catalyst for producing a cycloolefin by partial hydrogenation of a monocyclic aromatic hydrocarbon, wherein a porous zirconia material serving as a carrier is constituted from particles having an average primary particle diameter in a range of from 3 to 50 nm and an average secondary particle diameter in a range of from 0.1 to 30 μm.

(10) A production process of a cycloolefin by partial hydrogenation of a monocyclic aromatic hydrocarbon, comprising partially hydrogenating the hydrocarbon in liquid phase in the presence of water, by using the catalyst according to any of the above-described (1) to (8).

(11) The production process according to the above-described (10), wherein a zinc compound or a zinc ion, or both, are present in the liquid phase.

Effect of the Invention

An active hydrogenation catalyst according to the present invention is supported on a zirconia carrier. The catalyst is characterized in that the particle diameter of the catalyst is defined. Unlike conventional catalysts, the present catalyst exhibits excellent performance. For example, there is no dissolution of the carrier under hydrothermal and acidic conditions, or conferral of a positive influence on diffusion within the catalyst of the cycloolefin undergoing reaction. Additionally, the catalyst has the ability to suppress peeling and agglomeration on the carrier of the supported active hydrogenation component. The present catalyst also improves handleability during separation and recovery of the solid catalyst. In comparison with conventional catalysts, using the active hydrogenation catalyst according to the present invention allows for the stable production of cycloolefins having high activity and high selectivity over a long period of time.

BEST MODE FOR CARRYING OUT THE INVENTION

The present invention will now be described in detail.

The active hydrogenation catalyst according to the present invention uses zirconia as a carrier, and has catalyst particles in which the primary particles have an average particle diameter of 3 to 50 nm. The secondary particles formed therefrom have an average particle diameter of 0.1 to 30 μm. More preferably, the primary particles have an average particle diameter of 4 to 20 nm, and the secondary particles formed therefrom have an average particle diameter of 0.2 to 10 μm.

The catalyst according to the present invention uses zirconia as the carrier because zirconia materials are very durable.

"Catalyst average primary particle diameter", as used in the present invention, indicates the average size of the single particles contained in the catalyst and the carrier. In addition, "average secondary particle diameter" refers to the size of a mass of agglomerated primary particles, and indicates the average value of the size of what is usually called an "agglomerate". The primary particles of the catalyst according to the present invention are formed from a granular catalyst component and single zirconia particles, and secondary particles are formed from those primary particles.

The size of the particles constituting the catalyst is an important design matter for improving the reactivity and stability of catalytic performance. The size of the particles also strongly influences the handleability of the catalyst. A catalyst structure defined by primary particle diameter and secondary particle diameter can control the pores of the catalyst from its structural characteristics. Such pore function improves the reaction selectivity of the desired product. For example, it exerts a positive influence on substance mobility of the reaction substrate. In addition, a catalyst in which the primary particle diameter and secondary particle diameter are defined according to the present invention exhibits greatly improved activity and catalyst life performance. For example, a catalyst in which the primary and secondary particle diameters are defined according to the present invention has high dispersion of the active catalyst component, securely fixes and holds the active catalyst component on the carrier, allows the active catalyst component to act effectively, and suppresses sintering of the active catalyst component.

If the catalyst average primary particle diameter is less than 3 nm, agglomeration of the catalyst tends to occur under hydrothermal and acidic conditions. Furthermore, agglomeration of the zirconia particles used as the carrier tends to progress, and the specific surface area of the catalyst decreases. The active catalyst component then becomes contained within the carrier, and single-particles, mobile agglomerates and the like form. As a result, the stability of the catalytic performance cannot be maintained. If the catalyst primary particle diameter is greater than 50 nm, the active catalyst component supported on the carrier and the co-catalyst component for improving selectivity tend to move. These components may form mobile agglomerates, causing catalytic activity and selectivity to deteriorate.

If the catalyst average secondary particle diameter is less than 0.1 μm, suitable pore volume and pore structure cannot be maintained. The active hydrogenation component supported on the secondary particle surface is thus exposed, causing a deterioration in catalytic activity and selectivity. Furthermore, handleability, such as separation and recovery of the catalyst, worsens. Increasing the catalyst secondary average particle diameter to more than 30 μm results in a negative impact on intra-pore diffusion of the reaction substrate during cycloolefin production, and reactivity deteriorates. Furthermore, problems with catalyst shape-stability and handleability also occur. For example, the catalyst becomes more susceptible to pulverization under the conditions used.

The catalyst according to the present invention exhibits an advantageous effect wherein the particle diameter of primary particles and secondary particles which constitute the catalyst control movement of the substrate undergoing reaction within the catalyst. Additionally, the particle diameters also play a part in fixing the active catalyst component in the catalyst on the carrier. The geometrical action which occurs when primary particles agglomerate to form a secondary particle realizes high selectivity and high activity, while suppressing peeling, movement and agglomeration of the supported active catalyst component. Thus, the catalyst particle diameters improve stability. Further, if the catalyst particle diameters have the physical properties of said range, additional effects are produced. For example, it is more difficult for the secondary particles to fragment under the conditions used, the catalyst sedimentation rate increases, and the carrier is more easily separated and recovered from the reaction layer.

In the present invention, although the primary particle diameter of the catalyst is defined in terms of average particle diameter, the catalyst primary particles need not be particles of a uniform size, and particle size distribution is not restricted. The particle size distribution of the primary particles can be broad, and the particle size distribution does not have to be uniform. For example, particles having a primary particle diameter of 30 nm or more and particles having a primary particle diameter of 4 nm or less can be mixed together.

The pore structure of the catalyst according to the present invention possesses an average pore diameter in the range of from 2.5 to 15 nm. The pore volume in this pore diameter range is such that the catalyst is preferably 50% or more, by volume, of the total pore volume of pore diameters 2 to 150 nm. More preferably, the catalyst possesses an average pore diameter in the range of from 3 to 10 nm, and the pore volume in this pore diameter range is such that the catalyst is preferably 50% or more, by volume, of the total pore volume of pore diameters 2 to 150 nm.

Pore characteristics of a supported catalyst have an effect on control of particle growth of the supported active hydrogenation component. Additionally, the pore characteristics influence intra-pore mass transfer of the raw material substances and generated product during the reaction. If the average pore diameter is 2.5 nm or less, however, mass transfer of the reaction substrate does not occur effectively. As a result, selectivity and activity tend to deteriorate. Further, this very often leads to a situation where the active hydrogenation component is not stably dispersed on the carrier, and catalyst life is shortened. If the average pore diameter is larger than 15 nm, the active catalyst component loaded in a dispersed state sinters because of high-temperature and hydrothermal conditions or similar. This large pore diameter is unfavorable because it results in decreased activity. Preferably, pore distribution is narrow and uniform within the distribution range.

The present invention may support a metal or a metal compound, or a mixture thereof as the hydrogenation active catalyst component on the zirconia carrier. Components capable of hydrogenation catalysis are well-known in the conventional art. Ruthenium is particularly preferable among hydrogenation active catalyst components.

"Ruthenium", as mentioned in the present invention, includes ruthenium metal, ruthenium compounds and the like. It is used under conditions including a metal or a charged state, or a state possessing both characteristics. The average crystallite diameter of the supported ruthenium is preferably from 2 to 15 nm, as this diameter of ruthenium results in improved stability in the carrier pore interior. With an average crystallite diameter of less than 2 nm, movement within the carrier pores tends to occur, and agglomeration of the active hydrogenation component progresses. As a result, catalytic performance cannot be stably maintained. If the average crystalline diameter exceeds 15 nm, dispersion is poor, and activity with respect to the active catalyst component is also poor. Thus, the size of the pore diameter and active component being of the same order as that of the catalyst primary particle diameter improves the stability and activity of catalytic performance.

The amount of ruthenium supported on the carrier is preferably in the range of 2 to 30% by weight of the carrier weight converted into ruthenium metal. It is more preferable to have an amount of ruthenium in the range of from 4 to 22% by weight. The amount of ruthenium most preferable is in the range of from 8 to 18% by weight. If the amount of ruthenium is under 2% by weight, although activity increases with respect to active catalyst component, activity with respect to catalyst deteriorates. Thus, the total catalyst content, including the carrier, has to be increased. While the amount of the active catalyst component actually used can be decreased, this is not preferable. When the amount of active catalyst component is decreased, the catalyst becomes more susceptible to the impact of toxic substances stemming from the raw materials or the reactor material. On the other hand, if the active hydrogenation component exceeds 30% by weight, it becomes more difficult to carry out uniform support in practice.

The present invention can use, as a component which is supported on the carrier, ruthenium alone, or another co-supported metal component in addition to ruthenium. Examples of raw materials for the ruthenium supported on the carrier include halides, nitrates and hydroxides of ruthenium, ruthenium carbonyl and ruthenium complexes such as ruthenium amine complexes.

Further, examples of the component which can be used for co-supporting with ruthenium include zinc, nickel, iron, copper, cobalt, manganese, alkaline-earth elements, and rare-earth elements such as lanthanum, cerium, samarium and terbium. The raw material for these examples includes the various compounds of the co-supporting component, such as halides, nitrates, acetates and sulfates of the respective metal, and complexes containing the respective metal. These co-supporting components with ruthenium provide effects in reaction activity and selectivity performance of the catalyst. Additionally, they have an effect on the stability of catalyst life. Among them, zinc is a most preferable co-supporting component. Preferably, the content thereof is 5 moles or less of zinc atoms per 1 mole of ruthenium atoms, and the range of from 0.01 to 3 moles is particularly preferable.

The specific surface area of the catalyst according to the present invention is preferably in the range of from 20 to 300 $m^2/g$. A specific surface area in the range of from 30 to 150 $m^2/g$ is more preferable, and the range of from 50 to 120 $m^2/g$ is most preferable. To maintain a high dispersion of active hydrogenation component, a preferable range for the specific surface area exists. Within that range, the reaction stability of the catalyst can be maintained.

The present invention is characterized by using an interstitial-pore type porous zirconia material as its carrier for the catalyst. In the zirconia material, the average particle diameter of the primary particles and the average particle diameter of the secondary particles are defined. The meaning of "carrier average primary particle diameter", as used in the present invention, refers to the average size of zirconia single particles which constitute the carrier. In addition, "average secondary particle diameter" refers to the size of a mass of agglomerated primary particles, and indicates the average value of the carrier particle size (agglomerate size). "Interstitial-pore type porous zirconia material" refers to zirconia comprising a large number of pores which are formed as gaps between the primary particles. These pores are produced when the zirconia primary particles (single particles) agglomerate to create a secondary particle.

The carrier according to the present invention is an interstitial-pore type porous zirconia material constituted from secondary particles in which primary particles have agglomerated. The carrier serves to disperse the catalyst component, to fix and hold the catalyst component on the carrier, to allow the catalyst activity site to work effectively, and greatly contributes to improving activity and catalyst life performance by suppressing sintering and the like. Pore action of the carrier also has a large effect on reaction selectivity of the desired product, such as by exerting an influence on substance mobility of the reaction substrate.

When preparing a solid catalyst, the size of the particles constituting the carrier is an important design consideration for improving the reactivity and stability of catalytic performance. Size also has a strong effect on the handleability of the catalyst.

By defining the size of the zirconia primary particles and secondary particles which constitute the carrier, the supported active hydrogenation component exhibits excellent performance. For example, it suppresses peeling from the carrier and agglomeration on the carrier. The strength with which the supported component is fixed to the carrier reflects the size of the particles which constitute the carrier. The geometrical action which occurs when primary particles agglomerate to form a secondary particle contributes to an improvement in stability.

By using a porous zirconia material, which has its physical properties defined according to the present invention, as a carrier, catalyst physical properties can be achieved which approximate the physical properties of the carrier, and preferable physical properties as a catalyst can be maintained. The reason for this is that the porous zirconia material used in the present invention has high chemical resistance and is not readily affected by heat, and the physical properties of the carrier are not readily susceptible to a large changes due to subjecting the active catalyst component to the support process. The particle diameter of the active catalyst component supported on the porous zirconia material is minute. Thus, by preparing the amount of component to be supported in the range of 3 to 30% by weight, the physical properties of the carrier supporting the active catalyst component dramatically affect the physical property values of the catalyst. Therefore, the primary particles and secondary particles of the porous zirconia material used as the carrier are present without great change even after the preparation of the catalyst. The physical properties, such as particle size of the catalyst, are approximately the same value as those of the porous zirconia material used as the carrier.

The carrier used in the present invention is a porous zirconia material constituted from particles having an average primary particle diameter of 3 to 50 nm, and an average secondary particle diameter of 0.1 to 30 μm. More preferably, the porous zirconia material is constituted from particles having an average primary particle diameter of 4 to 20 nm, and an average secondary particle diameter of 0.2 to 10 μm.

If the average primary particle diameter is small, agglomeration of the zirconia particles tends to proceed under hydrothermal and acidic conditions. As a result, the specific surface area of the carrier decreases, the catalyst component becomes contained within the carrier single-particles and mobile agglomerates and the like form. As a result, the stability of the catalytic performance cannot be maintained. If the particle diameter is too large, the active hydrogenation component loaded within the pore and the co-catalyst component for improving selectivity tend to move and agglomerate. This leads to a deterioration in catalytic activity and selectivity. Thus, the primary particle diameter influences the stability of the physical properties of the carrier, as well as the stability of the component supported on the carrier.

In the present invention, while the primary particle diameter of the carrier is defined in terms of average particle diameter, the carrier primary particles need not be uniform particles, and particle size distribution of the primary particles is not restricted. The particle size distribution of the primary particles can be broad, and the particle size distribution does not have to be uniform. For example, particles having a size of 50 nm or more and particles having a primary particle diameter of 3 nm or less can be mixed together.

On the other hand, if the average secondary particle diameter is less than the above-described range, suitable pore volume and pore structure cannot be maintained. The active hydrogenation component supported on the secondary particle surface is exposed, and results in a deterioration in catalytic activity and selectivity. Furthermore, handleability, such as separation and recovery of the catalyst, worsens. If the secondary average particle diameter increases and exceeds the above-described range, intra-pore diffusion of the reaction substrate during cycloolefin production is negatively impacted, and reactivity deteriorates. Furthermore, problems with catalyst shape-stability and handleability also occur. For example, the catalyst becomes more susceptible to pulverization under the conditions used.

The porous zirconia material according to the present invention is an interstitial-pore type porous material, having secondary particles formed from an agglomeration of primary particles. As the pore characteristics of such porous material, the average pore diameter is in the range of from 2.5 to 15 nm, wherein the pore volume in this pore diameter range is such that the porous zirconia material is preferably 50% or more, by volume, of the total pore volume of pore diameters 2 to 150 nm.

Pore characteristics in a supported catalyst have an impact on controlling particle growth of the supported active catalyst component, and influence intra-pore mass transfer of the raw material substances and generated product during the reaction. While a carrier for a catalyst component is still feasible when the average pore diameter is less than 2 nm, this is not preferable because the intra-pore mass transfer of raw material substances and the generated product is restricted, resulting in deterioration in the reaction activity and selectivity. If the average pore diameter is large and exceeds the above-described range, the dispersibly supported catalyst component sinters because of high-temperature and hydrothermal conditions or similar. This large pore diameter is unfavorable because it results in decreased activity. Preferably, pore distribution is narrow and uniform within the distribution range.

To maintain the catalyst supported amount in a preferable range, the pore volume of the porous zirconia material according to the present invention is preferably a pore volume of 0.1 cm$^3$/g or more per 1 g of carrier. The pore volume is important in maintaining the carrier amount of the catalyst component in the preferable range, and more preferably within the range of 0.15 to 0.6 cm$^3$/g. Under a pore volume of 0.1 cm$^3$/g, only a minute amount of the active hydrogenation component can be supported in the pores. On the other hand, if the pore volume is too large, the pores and secondary particles are susceptible to physical destruction.

The specific surface area of the porous zirconia material according to the present invention is preferably in the range of from 20 to 300 m$^2$/g. More preferable is a specific surface area in the range of from 30 to 150 m$^2$/g, and most preferable is in the range of from 50 to 120 m$^2$/g. If the specific surface area is less than 20 m$^2$/g, it is difficult to maintain a high dispersion of the active hydrogenation component, and the activity with respect to active hydrogenation component is reduced. On the other hand, if the specific surface area exceeds 300 m$^2$/g, the porous zirconia material has poor physical stability under long-term reaction conditions, and it is difficult to stably maintain the synergetic effects of the ruthenium of the active hydrogenation component and the co-catalyst zinc.

The particle shape of the specific surface area of the carrier is simple and the surface roughness is small. When dispersed, a correlation between particle diameter and specific surface area can be obtained. In practice, however, they do not exactly match because the primary particles contain holes and cracks. These holes and cracks cause agglomeration and condensation among the particles. For this reason, the specific surface area of the carrier, which affects the degree of dispersion of the supported active catalyst component, is an important catalyst design indicator.

The porous zirconia material preferably possesses thermal stability. An index of the thermal stability is such that the weight loss during calcining at 250° C. is preferably not more than 10% of that prior to calcination. The porous zirconia material according to the present invention preferably includes hafnium oxide, and a preferable content thereof is from 0.2 to 5% by weight.

The porous zirconia material used as the carrier for the catalyst according to the present invention preferably possesses crystallinity in the same manner as commercially available products which are commonly used as ceramic materials or catalyst carriers. The effects of possessing crystallinity are that, in terms of crystallographic structure, the structure becomes stable and less susceptible to volumetric shrinkage of the pores. For these reasons, the supported active catalyst component can be stably held in the pores. As a result, catalyst deterioration under the reaction conditions is less likely to occur.

In addition to monoclinic systems, tetragonal systems, cubic systems and such similar systems exist for zirconia crystal structures. Among these crystal structures, however, a monoclinic system is preferable. Because crystallization speeds up deterioration of the specific surface area and mechanical strength of the carrier, the degree of crystallization should not be too high. A preferable crystallinity of the zirconia should be one so that some crystals can be identified with respect to crystalline orientation, but others cannot be identified under observation at about 500,000 times magnification by transmission electron microscopy (TEM), and crystal peaks of zirconia can be observed under X-ray analysis.

Synthesis of the porous zirconia material according to the present invention can use a well-known conventional method, such as sedimentation method, a hydrolysis method or a hydrothermal method. For example, synthesis can be carried out by thermal processing of a zirconia sol obtained from hydrolysis through heating. Alternatively, synthesis can be carried out by neutralization by an alkaline chemical, such as ammonia or the like, of an aqueous solution of a water-soluble zirconium salt. Furthermore, a commercially-available zirconia sol can be employed as a raw material to yield a powder precursor by gelation using an acid or an alkali, or to yield a powder by subjecting to thermal processing.

Examples of the water-soluble zirconium salts that can be used in the present invention include zirconium chloride, zirconium acetate, zirconium oxalate, potassium hexafluorozirconate (IV), sodium hexafluorozirconate (IV), zirconium (IV) oxychloride, zirconium (IV) oxynitrate, zirconium (IV) nitrate, zirconium (IV) sulfate and the like.

The size and shape of the zirconia particles can be controlled by the formation conditions, such as the solution concentration, PH, temperature and the like at the time of synthesis. Generally speaking, methods can be employed for controlling primary particle diameter by using liquid-phase processing at a temperature of 200° C. or less for several hours to several minutes. Methods can also be employed for controlling secondary particle diameter under liquid-phase or gas-phase at a temperature of 800° C. or less. However, a negative impact on catalytic performance may result if the secondary particles are synthesized by agglomeration of primary particles under acidic conditions. Thus, it is preferable to synthesize the secondary particles under neutral conditions or alkaline conditions, or to subject the primary particles to a thorough washing treatment prior to agglomeration.

The zirconia used as the carrier is preferably of high purity, as the inclusion of organic matter or minerals in the agglomerate of the carrier particles leads to a decrease in catalytic performance. Conventional processes which employ a template (for example, JP-A-5-254827 and the process disclosed in "Studies in Surface Science and Catalysis", 143, pp. 1035-1044 (2002)) are processes which construct zeolite-type or wormhole-type pores in the carrier. However, these processes have problems with the constructed pore attributes and the removal of the template. Thus, as these processes are not suitable, as the carrier design required for the present catalyst is difficult, and the pore design and interstitial-pore type porous material formed from agglomeration of the primary particles according to the present invention is technologically different. A catalyst which uses as a zirconia carrier obtained under a preparation process employing a template does not always have sufficient long-term stability under hydrothermal and acidic conditions. Further, when such a preparation process is used, a deterioration in catalytic performance, such as cycloolefin selectivity or catalytic activity, can be observed.

A process which is generally used for a supported catalyst preparation process can be used as the process for supporting the active catalyst component on the carrier. Since, in terms of achieving high activity, it is important to thoroughly disperse the catalyst component in the carrier, it is preferable to use a process which fixes to the carrier walls. For example, preferable processes include impregnating or adsorbing the catalyst component into the carrier pores or surfaces.

Alternatively, processes such as an evaporating-to-dryness process, a liquid-phase adsorption process, a dipping process, a pore-filling process, a spray process and the like, can be preferably employed using a solution in which a ruthenium compound is dissolved in a suitable solvent. For a co-precipitation process or mixing process, however, thorough dispersion of the catalyst component and realization of high-performance catalytic performance are difficult, even if limits are not placed on the pore volume of the carrier, the surface area, or the supported amount of active catalyst component. When co-supporting zinc and ruthenium, they may be supported separately or may be supported simultaneously. The zinc and ruthenium supported on the carrier are preferably located in proximity to each other.

Thus, the ruthenium-containing active catalyst component which is dispersibly supported on the carrier is subjected to reduction treatment in gas phase or liquid phase. Conventional well-known reducing agents, such as hydrogen, hydrazine, formalin, sodium borohydride, formic acid and the like, can be used as the reducing agent. Hydrogen or hydrazine can be preferably used. Further, reduction may also be carried out prior to charging the catalyst into the reaction system, carried out after charging in the reaction system, or carried out during the reaction. The reduction temperature is usually between 50 and 450° C., and preferably from 80 to 250° C.

It is thought that several factors contribute to the solid catalyst of the present invention being able to maintain long-term catalytic performance with higher activity and higher selectivity than that of conventional catalysts as a monocyclic aromatic hydrocarbon partial hydrogenation catalyst. Such factors include the carrier being stable, even under hydrothermal and acidic reaction conditions; the active hydrogenation component being uniformly and highly dispersibly supported in the pores of the carrier; the catalyst not being susceptible to catalyst degradation from sintering, even under hydrothermal conditions, due to the fact that the active catalyst component of the pores is firmly adhered to the carrier; and less susceptibility to poisoning effects than conventional low support-ratio catalysts since the amount of catalyst supported per 1 g of carrier can be increased.

As the type of usage for the catalyst according to the present invention, processes that employ common solid catalysts may be used. Such processes include a slurry-suspension process or a fixed-bed flow process employing the catalyst as a molded catalyst. In the present invention, water is required to be present in the reaction system. While the water content depends on the reaction form, usually water of from 0.01 to 100 times the weight of the monocyclic aromatic hydrocarbon can be used. It is preferable, however, that the liquid phase which comprises organic material, in which the raw materials and the generated product are the main constituents under the reaction condition, and water, forms a two-liquid phase. In practice, water is preferably from 0.5 to 20 times the weight of the aromatic hydrocarbon.

Further, in the present invention, a process can be used wherein a metal compound other than the catalyst component is present in the reaction system. Examples of such a metal compound include metal compounds of periodic law group 1 elements such as lithium, sodium and potassium; group 2 elements such as magnesium, calcium and strontium; rare-earth elements such as lanthanum, cerium, samarium and terbium; manganese, iron, nickel, cobalt, zinc, copper and the like. The kinds of metal compounds which can be used include carbonates, acetates, hydrochlorides, sulfates, nitrates, oxides and hydroxides.

The amount of these compounds present in the reaction system can be appropriately selected depending on the respective component characteristics and reaction form. The metal compound may be used singly or 2 or more kinds may be used simultaneously. The presence of zinc salts, in particular, greatly improves catalytic performance. As effective compounds thereof, zinc sulfate, zinc hydroxide and zinc oxide are preferable. Among these, zinc sulfate is most preferable. If an aqueous zinc sulfate is used, the concentration range is preferably within 0.1 to 30% by weight as zinc sulfate in the aqueous solution. In addition, basic zinc salts which are hardly soluble zinc compounds can also coexist as the zinc compound in the reaction system.

"Hardly soluble zinc compounds" indicates zinc salts which include a hydroxyl group or an oxygen atom which are considered as a separate negative constituent to the conjugate base residue of the various acids; or zinc compounds which do not readily dissolve in the reaction system. Examples include the double salt of zinc sulfate and zinc hydroxide. It is not necessary for these hardly-soluble zinc compounds to completely dissolve in the reaction system. The amount used when employing such a hardly-soluble zinc compound should be no more than 3 times the weight of the catalyst amount including the carrier. The metal compound present in the reaction system may completely exist as ions, exist as a compound, or in a state wherein the two are mixed.

In the present invention, the co-existing water phases are preferably reacted while being kept under neutral or acidic conditions. If a water phase becomes alkaline, the reaction rate dramatically decreases and, thus, is not preferable. A water phase PH of from 0.5 to less than 7 is preferable, and more preferable is from 2 to 6.5.

The "monocyclic aromatic hydrocarbon" which serves as a raw material to be used in the production process of a cycloolefin according to the present invention refers to benzene, toluene, xylene and lower-alkyl benzenes. The conditions for the partial hydrogenation reaction may be appropriately selected depending on the type and amount of the catalyst and additives to be used. The hydrogen pressure is from 0.1 to 20 MPa, and preferably from 1 to 10 Mpa. The reaction temperature is in the range of from 50 to 250° C., and preferably from 100 to 200° C. The reaction time can be appropriately selected by setting an actual goal for the selectivity and yield of the desired cycloolefin. Although there are no particular restrictions, the reaction time is usually from several seconds to several hours.

The present invention will now be explained in more detail by referring to examples; however, the present invention is in no way to be restricted to these examples. In addition, the evaluation methods of the various physical properties will be described in the following.

(Carrier Particle Diameter Measurement)

Measurement of the carrier particle diameter was carried out by observation using a Hitachi HD-2000 electron microscope and by using a Nikkiso Microtrac UPA. Measurement of the average primary particle diameter determined the length (Martin diameter) of segments that divided the projected area of the particles into two in a fixed direction, based on a projected image observed using an electron microscope. Specifically, the same number of each of 20 or more large, medium and small points were observed from a 500,000 times or more magnified projected image, wherein the number average diameter based on the measured results of a total of not less than 60 points was taken as the average primary particle diameter.

(Catalyst Particle Diameter Measurement)

Catalyst particle diameter measurement was carried out in the same manner as that for the above-described carrier particle diameter measurement.

(Average Ruthenium Crystallite Diameter Measurement)

Average ruthenium crystallite diameter measurement was measured using a Mac Science MPX18 X-ray diffractometer. Specifically, the half-width of the diffraction peak at a diffraction angle ($2\theta$) 44° of the ruthenium metal obtained from X-ray diffractometer measurement was measured, for determination using the Scherrer formula.

(Other Measurements)

Pore diameter, specific surface area and pore volume were measured using a Yuasa-Ionics Autosorb 3MP apparatus and selecting nitrogen as the adsorption gas. Specific surface area used desorption data obtained from the BET method. Pore diameter and pore distribution used desorption data obtained from the BJH method, and pore volume employed the adsorption data from P/P0 at Max. The catalyst metal composition was measured using Rigaku fluorescent X-ray analyzer. Measurement of the elution component in the reaction field was measured using a Rigaku JY-138-ICP emission analyzer.

(Catalyst Reaction Performance Evaluation)

Reaction evaluation was carried out using a batch method employing an autoclave, wherein reaction solution removed from time to time was analyzed using a gas chromatograph (GC-14B manufactured by Shimadzu Corporation) equipped with an FID detector. The below-described benzene conversion ratio and cyclohexene selectivity were calculated using the following calculation formulae (1) and (2) based on the experiment concentration analysis values.

[Expression 1]

$$\text{Benzene conversion ratio (\%)} = \frac{\text{Number of moles of benzene consumed in the reaction}}{\text{Number of moles of benzene supplied to the reaction}} \times 100 \quad (1)$$

[Expression 2]

$$\text{Cyclohexene selectivity (\%)} = \frac{\text{Number of moles of cyclohexene generated in the reaction}}{\text{Number of moles of cyclohexene generated in the reaction} + \text{Number of moles of cyclohexane generated in the reaction}} \times 100 \quad (2)$$

Further, "activity with respect to ruthenium" expresses the benzene conversion rate (g/Hr) with respect to Ru metal (g) contained in the catalyst, which was calculated using the following calculation formula (3) with a conversion ratio of 50% as a reference.

[Expression 3]

$$\text{Activity with respect to Ru 1 g} = \frac{\text{Used benzene amount (g)}}{2 \times \text{Time (Hr) taken to reach conversion of 50\%} \times \text{Used Ru amount (g)}} \quad (3)$$

Example 1

(1) Porous Zirconia Material Synthesis

While stirring 500 g of a hafnium oxide-containing zirconia sol (nitric acid stabilizer-solution with a 10 wt % zirconia content; manufactured by Newtecks Co., Ltd.) at 40° C., 25% ammonia water was slowly charged thereto. This solution was stirred for 1 hour under heating at 80° C., and then subjected to reduced-pressure drying at 90° C. using an evaporator to thereby form a solid. This mass of solidified powder was ground, then, using 0.5 N sodium hydroxide, mixed under stirring into an aqueous alkali solution for 1 hour at 60° C. The resulting solution was then repeatedly washed with water and filtered. The resulting filtrate was then dried at 110° C. using a vacuum dryer, which was then calcined at 250° C. to yield 47 g of a white powder. Results of measurement of the specific surface area and pore distribution of this white powder using a nitrogen adsorption and desorption method showed 1.5 wt % hafnium oxide-containing zirconia which had a specific surface area of 229 m²/g The pore volume was 0.31 cm³/g and the average pore diameter was 3.5 nm. The pore volume of pore diameters 2.5 to 15 nm was 85.1% by volume of the total pore volume of pore diameters 2 to 150 nm. It was learned from observation using an electron microscope and particle size distribution measurement that the physical properties of the powder were an average primary particle diameter of 4.7 nm and an average secondary particle diameter of 2.3 μm.

(2) Catalyst Preparation

An aqueous solution in which 8.9 g of zinc nitrate was dissolved was charged with 20 g of the hafnium oxide-containing zirconia porous material obtained above, which solution was then subjected to reduced-pressure drying at 80° C. using an evaporator. After calcining the resulting product for 2 hours at 350° C. and supporting a zinc component thereon, the product was subjected to, in order, alkali treatment, washing and drying in the same manner as the porous zirconia material. The resulting powder was charged in an aqueous solution containing 22.24 g of aqueous ruthenium chloride (9.99% by weight ruthenium content solution) in distilled water, wherein after a supporting operation of the ruthenium component was carried out in the same manner as the zinc support described above. The resulting product was then reduced under a hydrogen atmosphere at 200° C., to thereby yield a catalyst having a solid weight of 17 g. Analysis of this catalyst using an X-ray diffractometer showed an average crystallite diameter of the ruthenium of 2.5 nm. The results of measurement of the ruthenium and zinc content using a fluorescent X-ray analyzer are shown in Table 1. Measurement of the catalyst properties other than those described above was carried out in the same manner as that for the physical property measurement of the porous zirconia material, wherein primary particles were 5.5 nm and secondary particles were 2.3 μm. Average pore diameter was 3.5 nm and the pore volume of pore diameters 2.5 to 15 nm was 86.7% by volume of the total pore volume. It was also learned that the catalyst had a specific surface area of 201 m²/g.

(3) Benzene Partial Hydrogenation

A 1 liter autoclave was charged with 2 g of the above-described solid catalyst and 280 ml of an aqueous 10% by weight zinc sulfate solution, and purged with hydrogen while stirring. The temperature was raised to 150° C., and then hydrogen was further added under pressure to give a total pressure of 5 MPa. The resulting solution was left in this state for 22 hours then subjected to reaction pre-processing of the catalyst slurry. The autoclave pressure was subsequently once lowered to 3 MPa, then 140 ml of benzene were added under pressure along with hydrogen. The resulting solution was reacted under high-speed stirring at a total pressure of 5 MPa. Reaction solution was removed from time to time to obtain reaction selectivity and activity from the results of analysis of the liquid-phase composition by gas chromatography. Cyclohexene selectivity and the activity with respect to ruthenium when the ratio of benzene conversion was 50% are shown in Table 1. The post-reaction catalyst was removed from the autoclave, whereupon results of X-ray analysis showed that the ruthenium average crystal diameter was 2.7 nm, which was almost unchanged from that before reaction.

Example 2

A hafnium oxide-containing porous zirconia material was synthesized in the same manner as that of (1) in Example 1, except that 45 g of white powder was yielded by charging the above-describe zirconia sol into a 1 liter autoclave, wherein the synthesis time was extended to 10 hours at 120° C., and the calcining conditions were changed to 400° C. Results of measurement of the specific surface area and pore diameter of this white powder using a nitrogen adsorption and desorption method showed a specific surface area of 109 m$^2$/g, a pore volume of 0.34 cm$^3$/g, and an average pore diameter of 5.9 nm. The pore volume of pore diameters 2.5 to 15 nm was 66.4% by volume of the total pore volume of pore diameters 2 to 150 nm. It was learned from observation using an electron microscope and particle size distribution measurement for seeing the particle structure of this powder that the physical properties of the powder were an average primary particle diameter of 10.1 nm and an average secondary particle diameter of 4.1 μm. Next, using this hafnium oxide-containing porous zirconia material, a catalyst was prepared using the same catalyst preparation process as that of (2) in Example 1. The primary particles of this catalyst were 9.5 nm and the secondary particles were 3.9 μm. The average pore diameter was 6.2 nm, and the pore volume of pore diameters 2.5 to 15 nm was 61.7% by volume of the total pore volume. It was also learned that the catalyst had a specific surface area of 111 m$^2$/g. Furthermore, using this catalyst, after pre-processing of the catalyst in the same manner as that in (3) of Example 1, a reaction evaluation was performed. The ruthenium content and zinc content of the prepared catalyst, and the reaction results are shown in Table 1. The pre- and post-reaction ruthenium average crystallite diameter were 2.6 nm, wherein no change was observed.

Example 3

A 1 liter autoclave was charged with 4 g of the solid catalyst prepared in Example 2 and 280 ml of an aqueous 10% by weight zinc sulfate solution, and purged with hydrogen while stirring. The temperature was raised to 170° C., and then hydrogen was further added under pressure to give a total pressure of 5 MPa. The resulting solution was left in this state for 140 hours then subjected to reaction pre-processing of the catalyst slurry. The autoclave temperature was subsequently lowered to 150° C. and the pressure to 3 MPa, then 140 ml of benzene were added under pressure along with hydrogen. The resulting solution was reacted under high-speed stirring at a total pressure of 5 MPa. Reaction solution was removed from time to time to obtain the analysis of the oil-phase composition by gas chromatography. Cyclohexene selectivity and the activity with respect to ruthenium were measured when the ratio of benzene conversion was 50%. The reaction results are shown in Table 1. The post-reaction catalyst was removed from the autoclave, whereupon results of X-ray diffraction showed that the ruthenium average crystallite diameter was 2.8 nm, which was almost unchanged from that before reaction.

Comparative Example 1

(1) Porous Zirconia Material Synthesis

A mixed solution containing 140.1 g of 70% zirconium tetrapropoxide (manufactured by Aldrich Corp.), 150 ml of ethanol and 6 ml of acetyl acetone was slowly dropped under stirring into a solution containing 150 ml of distilled water, 150 ml of ethanol and 32.7 g of cethyltrimethyl ammonium bromide. The resulting solution was thoroughly mixed under stirring at room temperature, and left to stand. This resulting solution was transferred into an autoclave, stirred at 120° C., then filtered and washed. After drying, the resulting mixture was washed with ethanol, and again dried to yield 28.8 g of a white powder. Results of measurement of the specific surface area and pore distribution of this white powder using a nitrogen adsorption and desorption method showed a specific surface area of 501 m$^2$/g, a pore volume of 0.93 cm$^3$/g, and an average pore diameter of 6.7 nm. The pore volume of pore diameters 2.5 to 15 nm was 38.1% by volume of the total pore volume of pore diameters 2 to 150 nm. It was learned from observation using an electron microscope and particle size distribution measurement that the physical properties of the powder were an average primary particle diameter of 2.2 nm and an average secondary particle diameter of 2.5 μm.

(2) Catalyst Preparation and Benzene Partial Hydrogenation

Using the above-described porous zirconia material, a catalyst was prepared using the same catalyst preparation process as that of (2) in Example 1. The primary particles of this catalyst were 4.3 nm and the secondary particles were 7.9 μm. The average pore diameter was 26.9 nm, and the pore volume of pore diameters 2.5 to 15 nm was 32.2% by volume of the total pore volume. It was also learned that the catalyst had a specific surface area of 205 m$^2$/g and that the physical properties had clearly changed from those of the pre-catalysis porous zirconia material. Using the catalyst, pre-processing of the catalyst slurry was carried out in the same manner as that in Example 3, and the reaction was evaluated. In contrast to the pre-reaction ruthenium average crystallite diameter of 2.5 nm, post-reaction ruthenium average crystallite diameter was 5.5 nm, whereby it was clear from these results that the ruthenium average crystallite diameter had increased. The ruthenium content and zinc content of the prepared catalyst, and the reaction results are shown in Table 1.

Comparative Example 2

Catalyst preparation was carried out in the same manner as that of (2) in Example 1, except that zirconia from Kojundo Chemical Laboratory Co., Ltd., was made to serve as the carrier. Reaction evaluation was performed using the same methods as those of Example 3. The reaction results are shown in Table 1. The physical properties of the used zirconia and catalyst analysis were also measured in the same manner as that described above. The results were a zirconia specific surface area of 13 m$^2$/g, a pore volume of 0.19 cm$^3$/g, and an average pore diameter of 56.5 nm. The pore volume of pore diameters 2.5 to 15 nm was 3.4% by volume of the total pore volume of pore diameters 2 to 150 nm. It was learned from observation using an electron microscope and particle size distribution measurement that the physical properties of the powder were an average primary particle diameter of 82.3 nm and an average secondary particle diameter of 9.5 μm. Results of measurement of the physical properties after catalyst preparation showed an average primary particle diameter of 59.5 nm and an average secondary particle diameter of 6.6 μm of this catalyst. In addition, the average pore diameter was 49.9 nm, wherein the pore volume of pore diameters 2.5 to 15 nm was 5.8% by volume of the total pore volume. Specific surface area was 19 m$^2$/g. Results of measurement of the post catalysis ruthenium average crystallite diameter using an X-ray diffractometer were 4.6 nm. The catalyst after reaction was recovered. The ruthenium average crystallite diameter was 6.5 nm. That is, it was learned that the ruthenium was subjected to sintering in the reaction field.

Comparative Example 3

Catalyst preparation was carried out in the same manner as that of (2) in Example 1, except that zirconium hydroxide from Kojundo Chemical Laboratory Co., Ltd., was made to serve as the carrier. The catalyst was evaluated through reaction according to the same procedure as those of Example 3. The reaction results are shown in Table 1. In addition to measurement of the specific surface area and pore distribution of the zirconium hydroxide obtained in the same manner as that described above, the post-catalysis ruthenium and zinc were also measured for their content. The results were a specific surface area of 313 $m^2/g$, a pore volume of 0.36 $cm^3/g$, and an average pore diameter of 4.8 nm. The pore volume of pore diameters 2.5 to 15 nm was 48.6% by volume of the total pore volume of pore diameters 2 to 150 nm. From the catalyst analysis results, the average crystallite diameter of post-catalysis ruthenium was measured at 2.8 nm. The post-reaction catalyst was recovered, wherein the results of measurement of the ruthenium average crystallite diameter using an X-ray diffractometer were 2.9 nm, which had hardly changed.

Comparative Example 4

(1) Zirconia Surface-Modified Silica Porous Material Synthesis

A 1 liter beaker was charged with 200 g of distilled water, 160 g of ethanol and 20 g of cethyltrimethyl ammonium bromide, which were made to dissolve under stirring. The resulting solution was slowly charged with 85 g of tetraethyl ortho-silicate, thoroughly mixed under stirring, and left to stand at room temperature. The resulting solution was filtered, washed and then dried to obtain 22.1 g of a white powder by calcining at 550° C. Results of measurement of the physical properties of this white powder showed a specific surface area of 830 $m^2/g$ and a pore volume of 1.78 $cm^3/g$. Subsequently, 20 g of the above-described white powder was soaked in an aqueous solution in which 18 g of zirconium oxychloride octahydrate was dissolved. This solution was subjected to reduced-pressure drying using an evaporator and calcined at 600° C. to thereby synthesize a zirconia surface-modified silica porous material. Results of measurement of the specific surface area and pore distribution of the powder which had adsorbed this zirconia were a specific surface area of 510 $m^2/g$, a pore volume of 0.51 $cm^3/g$ and an average pore diameter of 3.7 nm. The pore volume of pore diameters 2.5 to 15 nm was 49.1% by volume of the total pore volume of pore diameters 2 to 150 nm. It was learned from observation using an electron microscope and particle size distribution measurement that the physical properties of the powder were an average primary particle diameter of 2.1 nm and an average secondary particle diameter of 8.4 μm.

(2) Catalyst Preparation and Benzene Partial Hydrogenation

Using the above-described zirconia surface-modified silica porous material, a catalyst was prepared using the same catalyst preparation process as that of (2) in Example 1, and this catalyst was used for reaction evaluation using the same method as that of Example 3. The pre-reaction physical properties of the catalyst were an average primary particle diameter of 4.3 nm and an average secondary particle diameter of 8.9 μm. The average pore diameter was 4.8 nm, and the pore volume of pore diameters 2.5 to 15 nm was 64.2% by volume of the total pore volume. Specific surface area was 251 $m^2/g$, while the average crystallite diameter of the ruthenium could not be measured from the X-ray diffraction image since it was 2 nm or less. The average crystallite diameter of the post-reaction ruthenium was 3.3 nm, whereby ruthenium crystal growth was observed. The ruthenium content and zinc content of the prepared catalyst, and the reaction results, are shown in Table 1.

TABLE 1

|  | Ru Loading (wt %) | Zn Loading (wt %) | Pre-processing Temperature (° C.) | Pre-processing Time (Hr) | Cyclohexene Selectivity (%) | Activity with Respect To Ru (Hr − 1) |
|---|---|---|---|---|---|---|
| Example 1 | 11.3 | 2.1 | 150 | 22 | 82.3 | 954 |
| Example 2 | 10.8 | 2.4 | 150 | 22 | 86.1 | 463 |
| Example 3 | 10.8 | 2.4 | 170 | 140 | 83.8 | 217 |
| Comparative Example 1 | 10.4 | 2.2 | 170 | 140 | 74.1 | 254 |
| Comparative Example 2 | 10.2 | 2.6 | 170 | 140 | 73.0 | 3 |
| Comparative Example 3 | 12.2 | 1.9 | 170 | 140 | 73.0 | 194 |
| Comparative Example 4 | 10.0 | 1.2 | 170 | 140 | 75.1 | 460 |

Example 4

A 200 ml polybeaker was charged with 5 g of the hafnium oxide-containing zirconia material synthesized in (2) of Example 1 and 100 g of an aqueous 10% by weight zinc sulfate solution, and stirred for 3 hours at 60° C. The stirred solution was then filtered using a 0.2 μm membrane filter, and the resulting filtrate was sampled to determine the zirconium elution amount contained in the filtrate. The results showed that the amount of zirconium in the aqueous solution was at the analytical method detection limits of 2 ppm or less. For comparison, 5 g of the zirconia surface-modified silica material synthesized in (1) of Comparative Example 4 were processed in the same manner to determine the silicon elution amount contained in that filtrate. Those results showed that the amount of silicon in the aqueous solution was 330 PPM.

Example 5

An aqueous solution of 14.8 g of lanthanum acetate hydrate dissolved in distilled water was charged with 20 g of the hafnium oxide-containing porous zirconia material used in Example 2. The resulting solution was dried under reduced pressure at 80° C., and then the dried residue was subjected to calcination for 5 hours at 400° C. The calcined solid contained 25% by weight of lanthanum in terms of the oxide. Subsequently, this was charged in an aqueous solution in which 22.24 g of an aqueous solution of ruthenium chloride (ruthenium 9.99% by weight content) was dissolved in distilled water. The ruthenium component was loaded by adsorption, and then washed at room temperature. The resulting product was then subjected to, in order, alkali treatment for 1 hour at 60° C., washing at room temperature, filtering and drying under reduced pressure at 110° C. After drying, the catalyst was not subjected to a reduction operation. The average primary particle diameter of this catalyst, which had not undergone a reduction operation, was 8.3 nm and the average secondary particle diameter was 3.3 μm. The average pore diameter was 5.1 nm, and the pore volume of pore diameters 2.5 to 15 nm was 60.5% by volume of the total pore volume. Specific surface area was 119 m²/g. Using this catalyst, after pre-processing of the catalyst using the same process as that of (3) of Example 1, the reaction was evaluated under the same conditions. The reaction results and the ruthenium content of the catalyst are shown in Table 2. The post-reaction catalyst was removed, and results of measuring the X-ray diffraction showed an average crystallite diameter of the ruthenium of 2.7 nm. Further, the average primary particle diameter of the recovered catalyst was 8.5 nm and the average secondary particle diameter of the same was 3.3 μm.

Comparative Example 5

A 10 L stainless steel vessel was charged with 5 kg of a zirconia sol (alkali stabilizer-containing solution with a 10 wt % zirconia content; manufactured by Newtecks Co., Ltd.), and then charged with a 5 wt. % aqueous solution of lanthanum acetate under stirring. After this solution was thoroughly stirred at room temperature, a spray dryer was used for spray drying, then the resulting powder was calcined to obtain 410 g of a white powder which supported 20% by weight of lanthanum by oxide conversion. This powder had a specific surface area of 64 m²/g, a pore volume of 0.32 cm³/g and an average pore diameter of 22.7 nm. The pore volume of pore diameters 2.5 to 15 nm was 18.6% by volume of the total pore volume of pore diameters 2 to 150 nm. It was learned from observation using an electron microscope and particle size distribution measurement that the average primary particle diameter was 17.8 nm, and an average secondary particle diameter for this powder was 53 μm. Using this powder, adsorption and support of the ruthenium was carried out in the same manner as Example 5. The average primary particle diameter of the catalyst was 4.3 nm and the average secondary particle diameter of the same was 53 μm. The average pore diameter was 31.5 nm, and the pore volume of pore diameters 2.5 to 15 nm was 20.1% by volume of the total pore volume. Specific surface area was 64 m²/g. This catalyst was subjected to catalyst pre-processing using the same method used in (3) of Example 1 for reaction evaluation under the same conditions. The results are shown in Table 2.

Example 6

A 1 liter Hastelloy autoclave was charged with 4 g of the solid catalyst prepared in Example 5 and 280 ml of an aqueous 10% by weight zinc sulfate solution, and purged with hydrogen under stirring. After the temperature was raised to 170° C., hydrogen was further added under pressure to give a total pressure of 5 MPa. The resulting solution was left in this state for 140 hours then subjected to reaction pre-processing of the catalyst slurry. The autoclave temperature was subsequently lowered to 150° C. and the pressure to 3 MPa, then 140 ml of benzene were added under pressure along with hydrogen, and the resulting solution was reacted under high-speed stirring at a total pressure of 5 MPa. Reaction solution was removed from time to time for analysis of the oil-phase composition by gas chromatography. Cyclohexene selectivity and the activity with respect to ruthenium when the ratio of benzene conversion was 50% were measured. The reaction results are shown in Table 2. Further, the post-reaction catalyst was removed from the autoclave, whereupon the results of measuring X-ray analysis showed that the ruthenium average crystallite diameter was 2.9 nm.

TABLE 2

| | Ru Loading (wt %) | Pre-processing Temperature (° C.) | Pre-processing Time (Hr) | Cyclohexene Selectivity (%) | Activity with Respect To Ru (Hr − 1) |
|---|---|---|---|---|---|
| Example 5 | 12.2 | 150 | 22 | 83.9 | 723 |
| Comparative Example 5 | 99 | 150 | 22 | 65.6 | 191 |
| Example 6 | 12.2 | 170 | 140 | 83.8 | 357 |

INDUSTRIAL APPLICABILITY

The present invention is useful as a catalyst for production of a cycloolefin which possesses high activity and high selectivity and in which catalyst life and handleability are improved.

The invention claimed is:

1. A catalyst for production of a cycloolefin by partial hydrogenation of a monocyclic aromatic hydrocarbon, wherein the catalyst comprises a porous zirconia material as a carrier and ruthenium as an active catalyst component, wherein said catalyst component is constituted from particles having an average primary particle diameter of said catalyst in a range of from 3 to 50 nm and an average secondary particle diameter in a range of from 0.1 to 30 μm, wherein the average crystallite diameter of the ruthenium is from 2 to 15 nm.

2. The catalyst according to claim 1, wherein the catalyst has an average pore diameter in a range of from 2.5 to 15 nm, and a pore volume in the 2.5 to 15 nm range of the pore diameter is 50% by volume or more of the total pore volume having pore diameters from 2 to 150 nm.

3. The catalyst according to claim 1, wherein the catalyst comprises zinc or a zinc compound.

4. The catalyst according to claim 1, wherein the catalyst has a specific surface area of from 20 to 300 m²/g.

5. The catalyst according to claim 1, wherein the carrier is an interstitial-pore type porous zirconia material formed by assemblage of the primary particles.

6. The catalyst according to claim 5, wherein the carrier is a hafnium oxide-containing zirconia.

7. A production process of a cycloolefin by partial hydrogenation of a monocyclic aromatic hydrocarbon, comprising partially hydrogenating the hydrocarbon in liquid phase in the presence of water, by using the catalyst according to claim 1.

8. The production process according to claim 7, wherein a zinc compound or a zinc ion, or both, are present in the liquid phase.

9. A production process of a cycloolefin by partial hydrogenation of a monocyclic aromatic hydrocarbon, comprising partially hydrogenating the hydrocarbon in liquid phase in the presence of water, by using the catalyst according to claim 2.

10. A production process of a cycloolefin by partial hydrogenation of a monocyclic aromatic hydrocarbon, comprising partially hydrogenating the hydrocarbon in liquid phase in the presence of water, by using the catalyst according to claim 1.

11. A production process of a cycloolefin by partial hydrogenation of a monocyclic aromatic hydrocarbon, comprising partially hydrogenating the hydrocarbon in liquid phase in the presence of water, by using the catalyst according to claim 3.

12. A production process of a cycloolefin by partial hydrogenation of a monocyclic aromatic hydrocarbon, comprising partially hydrogenating the hydrocarbon in liquid phase in the presence of water, by using the catalyst according to claim 4.

13. A production process of a cycloolefin by partial hydrogenation of a monocyclic aromatic hydrocarbon, comprising partially hydrogenating the hydrocarbon in liquid phase in the presence of water, by using the catalyst according to claim 5.

14. A production process of a cycloolefin by partial hydrogenation of a monocyclic aromatic hydrocarbon, comprising partially hydrogenating the hydrocarbon in liquid phase in the presence of water, by using the catalyst according to claim 6.

\* \* \* \* \*